(12) United States Patent
Burger

(10) Patent No.: US 6,318,374 B1
(45) Date of Patent: Nov. 20, 2001

(54) EPICARDIAL PACER WIRES SHIELD

(76) Inventor: Susan Burger, 454 Vivienne Dr., Watsonville, CA (US) 95076

( * ) Notice: Subject to any disclaimer, the term of this patent is extended or adjusted under 35 U.S.C. 154(b) by 0 days.

(21) Appl. No.: 09/435,328

(22) Filed: Nov. 5, 1999

(51) Int. Cl.⁷ .................................................. A61B 19/02
(52) U.S. Cl. .......................... 128/897; 607/115; 607/129; 607/152; 607/149; 206/438; 128/908; 600/386; 600/392
(58) Field of Search ............................ 607/1, 130, 115, 607/116, 119, 129, 149, 152, 153, 63; 600/372, 373, 374, 382, 384, 386, 388, 391, 392, 393; 128/897, 908, 918; 206/438

(56) References Cited

U.S. PATENT DOCUMENTS

| 4,290,567 | * | 9/1981 | Saito ..................................... 242/198 |
| 4,718,876 | * | 1/1988 | Lee ....................................... 446/295 |
| 5,033,474 | * | 7/1991 | Varelis et al. ......................... 128/696 |
| 5,427,243 | * | 6/1995 | Roshdy ................................. 206/438 |
| 5,466,244 | * | 11/1995 | Morgan ..................................... 607/5 |
| 5,503,266 | * | 4/1996 | Kalbfeld et al. ..................... 206/63.3 |
| 6,163,728 | * | 12/2000 | Wildon ................................. 607/132 |

* cited by examiner

Primary Examiner—Kennedy Schaetzle
(74) Attorney, Agent, or Firm—Jeffrey A. Hall

(57) ABSTRACT

An epicardial pacer wires shield comprising a base element with a pair of spools mounted to the base element. Each of spool of the pair of spools has a slit in a top surface thereof for securing the epicardial pacer wires to the spool. A cover element is configured to be secured to the base element, and has an adhesive layer on a back surface. A tab is mounted on an edge of the cover element for removing the cover element from the base element when the cover element and base element are secured together.

11 Claims, 1 Drawing Sheet

EPICARDIAL PACER WIRES SHIELD

BACKGROUND OF THE INVENTION

1. Field of Invention

This invention relates to shields for epicardial pacer wires, and more particularly to epicardial pacer wire shields which are applied directly to the chest wall and each epicardial pacer wire individually wound around a spool.

2. Description of the Related Art

Heretofore, numerous devices have been proposed and implemented for delivering electric pulses to the heart. One commonly used device is the epicardial pacemaker. Epicardial pacer wires are pacemaker leads usually made of Teflon insulated stainless steel and are inserted into the epicardial surface of the heart during coronary artery bypass surgery. These wires are sutured to the atrium and/or ventricle of the heart by the surgeon and then brought through the subcutaneous tissue of the chest wall.

Typically, epicardial pacer wires extend six to twelve inches, ending in a stiff, uninsulated tip. This tip is used for insertion into ventricular an/or atrial ports of a temporary pacemaker. This pacemaker is used prophylactically in the case of heart dysrhythmias. Through these epicardial pacer wires, the temporary pacemaker delivers an electrical charge in milliamps that stimulates and electrical response in the heart, causing a heartbeat. This temporary cardiac pacing has proven to be a significant lifesaving technique for post operative cardiac patients.

The epicardial pacer wires are typically knotted to prevent retraction of the wires back under the skin. To prevent minute electric shock through the exposed wires, they need to be protected. Further, as minute electric charges can be delivered to the heart through the epicardial wires, although usually not felt by the patient, such charges can cause lethal ectopy. Sources of minute electric charges are static electricity or ungrounded, unchecked electrical equipment, such as a hospital bed frame. To prevent such electrical shock, epicardial pacer wires need to be isolated by a clean, waterproof dressing or shield.

Accordingly, the present invention provides a novel epicardial pacer wires shield to safely protect the patient from electric shock through exposed epicardial pacer wires. The epicardial pacer wire shield of the present invention is easy to use, inexpensive to manufacture, reliable, and highly efficient at shielding the patient from exposed epicardial pacer wires.

Additional objects and advantages of the invention will be set forth in the description which follows, and in part will be obvious from the description, or may be learned by practice of the invention. The objects and advantages of the invention may be realized and obtained by means of the instrumentality's and combinations particularly pointed out in the appended claims.

BRIEF SUMMARY OF THE INVENTION

The present invention is a safe and reliable device for shielding a cardiac patient from shock from exposed pacer wires. The epicardial pacer wire shield of the present invention is easy to position and apply, and simple to remove when desired.

Accordingly, an epicardial pacer wires shield is provided, comprising a base element with a pair of spools mounted to the base element. Each spool of the pair of spools has a slit in a top surface thereof for securing the epicardial pacer wires to the spool. A cover element is configured to be secured to the base element, and has an adhesive layer on a back surface. A tab is mounted on an edge of the cover element for removing the cover element from the base element when the cover element and base element are secured together.

The epicardial pacer wire shield may be provided in a heart shape so as to distinguish it from other electrodes applied to the chest wall of patients, or in alternative embodiments provided in other geometrical configurations, such as rectangular, square, oblong, triangular, or the like.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

DETAILED DESCRIPTION OF THE INVENTION

Reference will now be made in detail to the present preferred embodiments of the invention as illustrated in the accompanying drawings.

In accordance with the present invention, there is provided an epicardial pacer wires shield having a base element with a pair of wire retaining spools mounted to the base element. Each spool of the pair of spools has a slit in a top surface thereof for securing epicardial pacer wires to the spool. A cover element is configured to be secured to the base element. The cover element preferably has an adhesive layer on a back surface. A tab is mounted on an edge of the cover element for removing the cover element from the base element when the cover element and base element are secured together.

Figure 1:
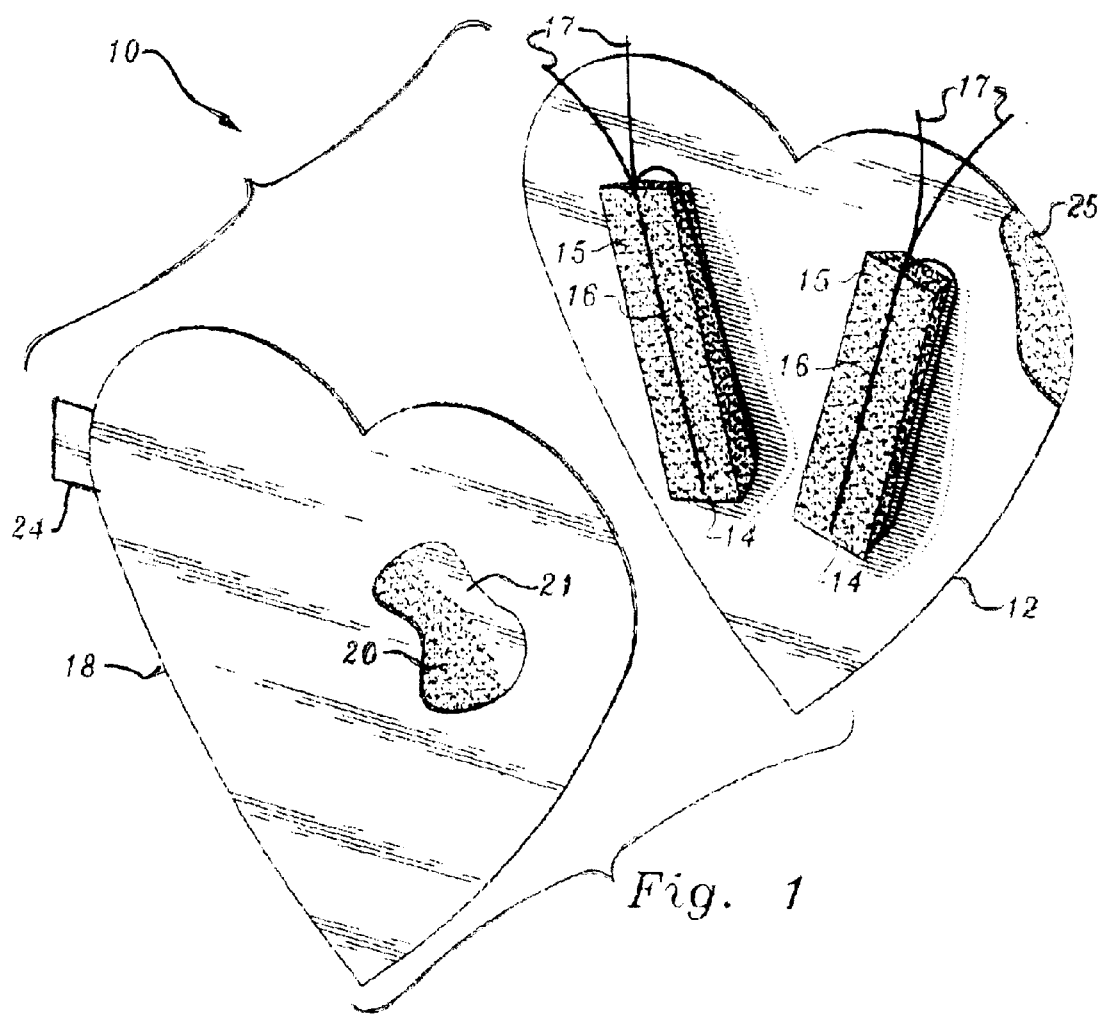
FIG. 1 is a perspective view of the epicardial pacer wire shield shown with the cover element separated from the base element, according to the invention.

In FIG. 1, an epicardial pacer wires shield 10 is shown according to a preferred embodiment of the invention. Shield 10 preferably includes a base element 12, and a pair of spools 14 mounted on base element 12 by adhesives or integrally formed therewith. Each of the pair of spools 14 has a slit 16 in a top surface 15 for securing epicardial pacer wires 17 therein. Preferably spools 14 are oblong in configuration, but alternatively may be configured as rectangular, circular, oval, or the like.

A cover element 18 is configured to be secured to base element 12. Cover element 12 is preferably provided with an adhesive layer 20 on back surface 22, and a removable paper cover 21. A tab 24 for removing cover element 18 from base element 12 is provided, and facilitates the removal of cover element 18 from base element 12 when desired.

Figure 2:
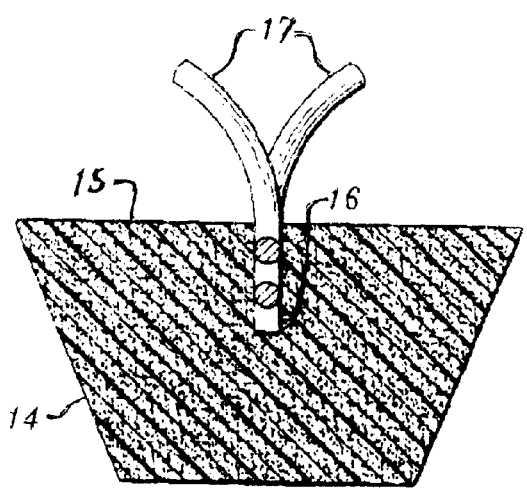
FIG. 2 is a sectional view of a wire retaining spool of such device, according to the invention.

As seen in FIGS. 1 and 2, base element 12 and cover element 18 are preferably heart shaped to easily distinguish shield 10 from other electrodes applied to the chest wall of a patient. Of course, shield 10 may be provided in other geometrical shapes if desired, such as rectangular, square, oval, triangular, or the like.

Preferably base element 12 is made of a synthetic foam rubber which has an adhesive backing 25. Shield 10 is applied directly to the chest wall of a patient and each epicardial pacer wire 17 is individually wound around a spool 14, which is also preferably composed of a synthetic foam rubber or plastic. After being wound around spool 14, the tips of epicardial pacer wires 17 are then placed into slit 16 on the top 15 of spool 14. Slit 16 recloses itself when manual pressure is applied and released, thereby holding epicardial pacer wires 17 in place. Epicardial pacer wires 17 are now safely housed and positioned and cover element 18, preferably composed of a synthetic foam rubber or plastic, is placed over base element 12 rendering the shield waterproof.

The configuration of base element 12 and cover element 18 are preferably thin, similar to a telemetry electrode patch. To prevent epicardial pacer wires 17 from slipping off spool 14, the preferred configuration, as seen in FIG. 2, is oblong with a central slit 16. Slit 16 in top surface 15 of spools 14, enable the user to insert the tips of the epicardial pacer wires using manual digital pressure. When digital pressure is released, the foam rubber closes upon itself, safely housing the wire tips. Cover element 18 is then folded over after paper backing 21 is removed, which exposes adhesive layer 20 which sticks to base element 12 when applied.

To enable the user of the epicardial pacer wires shield 10 to have instant access to wires 17 housed therein, the user need only pull up on tab 24 on cover element 18, which will remove cover element 18 from base element 12, allowing access to wires 17. Preferably tab 24 is made of paper or thin plastic. Once opened, epicardial pacer wires shield should be replaced with a new shield since the waterproof status has been breached.

As is evident from the above description, a wide variety of epicardial pacer wires shields may been envisioned from the device described herein and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. An epicardial pacer wires shield, comprising:

a base element;

a pair of spools mounted on said base element, each of said pair of spools having a slit in a top surface thereof; and a cover element, said cover element being configured to be secured to said base element, said cover element having an adhesive layer on a back surface thereof, and a tab for removing said cover element from said base element when the cover element and base element are secured together.

2. The epicardial pacer wires shield of claim 1, wherein said cover element has an adhesive backing.

3. The epicardial pacer wires shield of claim 1, wherein said base element is heart shaped.

4. The epicardial pacer wires shield of claim 1, wherein said cover element is heart shaped.

5. The epicardial pacer wires shield of claim 1, wherein said base is composed of foam rubber.

6. A protective, removable epicardial pacer wires shield, comprising:

a base element;

means for securing epicardial pacer wires to said base element; and a cover element, said cover element being configured to be secured to said base element, said cover element having an adhesive layer on a back surface thereof, and a tab for removing said cover element from said base element when the cover element and base element are secured together.

7. The epicardial pacer wires shield of claim 6, wherein said means for securing epicardial pacer wires to said base element comprise a pair of spools mounted on said base element, each of said pair of spools having a slit in a top surface thereof.

8. The epicardial pacer wires shield of claim 6, wherein said cover element has an adhesive backing.

9. The epicardial pacer wires shield of claim 6, wherein said base element is heart shaped.

10. The epicardial pacer wires shield of claim 6, wherein said cover element is heart shaped.

11. The epicardial pacer wires shield of claim 6, wherein said base is composed of foam rubber.

* * * * *